(12) United States Patent
Christiano

(10) Patent No.: US 8,008,471 B2
(45) Date of Patent: Aug. 30, 2011

(54) NUCLEIC ACIDS FOR INHIBITING HAIRLESS PROTEIN EXPRESSION AND METHODS OF USE THEREOF

(75) Inventor: Angela M. Christiano, West Orange, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 12/715,207

(22) Filed: Mar. 1, 2010

(65) Prior Publication Data

US 2010/0221318 A1  Sep. 2, 2010

Related U.S. Application Data

(60) Division of application No. 12/139,818, filed on Jun. 16, 2008, now abandoned, which is a continuation of application No. 10/122,013, filed on Apr. 12, 2002, now Pat. No. 7,423,022.

(60) Provisional application No. 60/283,618, filed on Apr. 13, 2001.

(51) Int. Cl.
*C07H 21/02* (2006.01)
*C07H 21/04* (2006.01)

(52) U.S. Cl. .................. 536/24.5; 536/23.1; 536/24.3; 536/24.33

(58) Field of Classification Search .............. 536/23.1, 536/24.3, 24.33, 24.5; 514/44
See application file for complete search history.

(56) References Cited

U.S. PATENT DOCUMENTS

| 6,348,348 | B1 | 2/2002 | Thompson |
| 6,812,339 | B1 * | 11/2004 | Venter et al. .............. 536/24.31 |
| 2009/0004169 | A1 * | 1/2009 | Christiano .................. 424/94.1 |

FOREIGN PATENT DOCUMENTS

WO  WO 9938965  8/1999

OTHER PUBLICATIONS

Chaley and Korotkov. (Molecular Biology, 2001 vol. 35, No. 6:1023-1031).*
Ahmad, Wasim et al. (1999) Genomic Organization of the Human Hairless Gene (HR) and Identification of a Mutation Underlying Congenital Atrichia in an Arab Palenstinian Family, *Genomics* 55: (2):141-148.
Sprecher, Eli et al. (1998) Atrichia With Papular Lesions Maps to 8p in the Region Containing the Human Hairless Gene, *American Journal of Medical Genetics* 80: 546-550.
Santorio, Stephen W. et al. (1997) A general purpose RNA-cleaving DNA enzyme, *Proc. Natl. Acad. Sci.* USA 94: 4262-4266.
Ahman, Wasim et al. (1998) Alopecia Universalis Associated with a Mutation in the Human Hairless Gene, *Science* 279: 720-724.

(Continued)

*Primary Examiner* — Sean McGarry
*Assistant Examiner* — Terra Cotta Gibbs
(74) *Attorney, Agent, or Firm* — Baker Botts L.L.P.

(57) ABSTRACT

The present invention provides DNAzymes and ribozymes that specifically cleave Hairless protein mRNA. The present invention also provides antisense oligonucleotides that specifically inhibit translation of Hairless Protein mRNA. The present invention also provides various methods of inhibiting the expression of Hairless Protein. Finally the invention provides pharmaceutical compositions containing the instant DNAzymes, ribozymes and antisense oligonucleotides as active ingredients.

6 Claims, 6 Drawing Sheets

OTHER PUBLICATIONS

Cichon, Sven et al. (1998) Cloning, genomic organization, alternative transcripts and mutational analysis of the gene responsible for autosomal recessive universal congenital alopecia, *Human Molecular Genetics* 7: 1671-1679.

Cserhalmi-Friedman et al. (2004) Experimental Dermatology 13(3): 155-162 Recapitulation of the Hairless Mouse Phenotype Using Catalytic Oligonucleotides: Implications for Permanent Hair Removal.

Cairns et al. (2000) Nucleic Acid Mutation Analysis Using Catalytic DNA. Nucleic Acids Res 28:E9.

Fedor M.J. (2000) Structure and Function of the Hairpin Ribozyme. J. Mol. Biol. 297 (2): 269-91.

Jen et al. (2000) Suppression of Gene Expression by Targeted Disruption of Messenger RNA: Available Options and Current Strategies. Stem Cells 18:307-319.

Santoro et al. (2000) RNA cleavage by a DNA enzyme with extended chemical functionality. J. Am. Chem. Soc. 122(11):2433-9.

Bartel D.P. (1999) Creation and evolution of new ribozymes. Biol. Bull. 196:322-3.

Long and Sullenger (1999) Evaluating group I intron catalytic efficiency in mammalian cells. Mol. Cell. Biol. 19: 6479-87.

Parthasarathy et al. (1999) Hammerhead ribozyme-mediated inactivation of mutant RET in medullary thyroid carcinoma. Cancer Res. 59:3911-4.

Santiago et al. (1999) New DNA enzyme targeting Egr-1 mRNA inhibits vascular smooth muscle proliferation and regrowth after injury. Nat. Med. 5(11):1264-1268. Nat. Med. 5(11):1264-69. Erratum 5(12):1438.

Ahmad et al. (1998) Molecular basis of a novel rhino (hr(rhChr)) phenotype: a nonsense mutation in the mouse hairless gene. Exp. Dermatol. 7:298-301.

Branch A. (1998) A Good Antisense is Hard to Find. Trends Biochem. Sci. 23:45-50.

Panteleyev et al. (1998) Molecular and functional aspects of the hairless (hr) gene in laboratory rodents and humans. Exp. Dermatol. 7:249-67.

Panteleyev et al. (1998) Molecular basis for the rhino Yurlovo (hr (rhY) ) phenotype:severe skin abnormalities and female reproductive defects associated with an insertion in the hairless gene. Exp. Dermatol. 7:281-8.

Phylactou et al. (1998) Ribozymes as therapeutic tools for genetic disease. Human Mol. Genet. 7:(10) 1649-53.

Santoro and Joyce (1998) Mechanism and utility of an RNA-cleaving DNA enzyme. Biochemistry 37:13330-42.

Vaish et al. (1998) Recent developments in the hammerhead ribozyme field. Nucleic Acids Res. 26:5237-42.

Bertrand et al. (1997) The expression cassette determines the functional activity of ribozymes in mammalian cells by controlling their intracellular localization. RNA 3:75-88.

Montgomery and Dietz (1997) Inhibition of fibrillin 1 expression using U1 snRNA as a vehicle for the presentation of antisense targeting sequence. Hum. Mol. Genet. 6:519-25.

Flory et al. (1996) Nuclease resistant ribozymes decrease stromelysin mRNA levels inn rabbit synovium following exogenous delivery to the knee joint. Proc. Natl. Acad. Sci. USA 93:754-758.

Matzura and Wennborg (1996) RNAdraw: an integrated program for RNA secondary structure calculation and analysis under 32-bit Microsoft Windows. Comput. Appl. Biosci. 12:247-9.

Michienzi et al. (1996) U1 small nuclear RNA chimeric ribozymes with substrate specificity for the Rev pre -mRNA of human immunodeficiency virus. Proc. Natl. Acad. Sci. USA 93:7219-7224.

Sioud M. (1996) Ribozyme modulation of lipopolysaccharide induced tumor necrosis factor- alpha production by peritoneal cells in vitro and in vivo. Eur. J. Immunol. 26:30 1026-1031.

Pley et al. (1994) Three-dimensional structure of a hammerhead ribozyme. Nature 372:68-74.

Sioud and Drlica (1991) Prevention of human immunodeficiency virus type 1 integrase expression in *Escherichia coli* by a ribozyme. Proc. Natl. Acad. Sci. USA 88: 7303-7.

Cech T.R. (1987) The chemistry of self-splicing RNA and RNA enzymes. Science 236:1532-9.

Cserhalmi-Friedman et al. Recapitulation of the Hairless Mouse Phenotype Using Catalytic Oligonucleotides: Implications for Permanent Hair Removal. Experimental Dermatology, 2004 vol. 13:155-162.

Dokka et al., J Invest Dermatol., 2005 vol. 124:971-975.

Nielsen, PE. Systemic delivery: The last hurdle? Gene Therapy, 2005 vol. 12: 956-957.

Sun et al. Catalytic Nucleic Acids: From Lab to Applications. Pharmacol Rev. 2000 vol. 52:325-347.

Cichon et al. Cloning, genomic organization, alternative transcripts and mutational analysis of the gene responsible for autosomal recessive universal congenital alopecia. Human Molecular Genetics, 1998 vol. 7: 1671-1679.

Panteleyev et al. Molecular and functional aspects of the hairless gene in laboratory rodents and humans. Experimental Dermatology, 1998 vol. 7:249-267.

Branch, A. A Good Antisense is Hard to Find. TIBS, Feb. 1998 vol. 23, pp. 45-50.

Jen et al. Suppression of Gene Expression by Targeted Disruption of Messenger RNA: Available Options and Current Strategies. Stem Cells, 2000, vol. 18:307-319.

Ahmad et al. Genomic Organization of the Human Hairless Gene and Identification of a Mutation Underlying Congenital Atrichia in an Arab Palestinian Family. Genomics, 1999 vol. 55: 1-9.

Santoro et al. A general purpose RNA-cleaving DNA enzyme. Proceedings of the National Academy of Sciences, 1997 vol. 94;4262-4266.

Milligan et al. Current Concepts in Antisense Drug Design. Journal of Medicinal Chemistry, 1993 vol. 36:1923-1937.

Weintraub, HM. Antisense RNA and DNA. Scientific American, 1990 pp. 40-46.

* cited by examiner

FIGURE 1A

```
tctcccggga gccactcccc tgggcgcctc tccagcccct gggctggaag caccagcaac    60
cctggggatg gggcagaccc tcacagcccg gggtctggag ccggtgtcgg agctcacatg   120
ggcccatgac ctctccagac atttggcaaa atcaaggccc ttagaccagg gacagaccca   180
agcccaggcc ctcccagagg tcataggacg caacccttttg tgcccttggg ctatggaaga   240
ggtttgggaa cggctttggg gtggaagatg gccaaaggag cagcttggcc aggtgaggat   300
gaggcagggc agacacaggc cagtggggcg tgccatgtgc cacagatgga gaggaccagg   360
agccagtggc ccggcaggca cagcccggtt ggcgtgggcc agagcgccca tcactgaccc   420
gtgagaactc gactgcccct gccagctctg gcactgcccc ctcccagccg cccgccctla   480
gcaccctggg gggcaccccg cccaaccgtg gctggtccg gccctcccg cctttgctc   540
cagttcccgg gcttggcacc tatagtgggg gtgccgcccg cctgccaggc tccggggccg   600
ggcccacggg agggtggggc ggctgggaag ctggcacgct gccccggggg agcctctgtc   660
ggcaggcgcc cgggtgccgc ggggggggagg gggaacaaag ggctcattct ccccgtgcgc   720
agccggtggc atcgccgggg cgttggcgga agccccgggg gccgggagg gggccggccc   780
aggcgcggcc gccgaatcac gggctcctgt ttcccgcagg gtgctggagg aggaaaccgg   840
cggagcagct tccccactct cagttgcgcg tctggcgatg gcgatcagag gtcgtgctgc   900
gctctccgcc gcgctctacc tccattagcc gcgctgcgcg gtgctgcgcc ctcgccggtg   960
cctctctcct gggtcccagg atcggccccc accatccagg cacgaccccc ttccccggcc  1020
cctcggcctt tcccccaact cggccatctc cgacccgggg cgcgtgttcc ccccggcccg  1080
gcgccttctc tccctccggg ggcaccgct ccctagcccc ggcccggcc tcccgcggc  1140
gcagcacgga gtctcggcgt cccatggcgc aacctacggc ctcggcccag aagctggtgc  1200
ggccgatccg cgccgtgtgc cgcatcctgc agatcccgga gtccgacccc tccaacctgc  1260
ggccctagag cgcccccgcc gccccggggg aaggagagcg cgagcgcgct gagcagacag  1320
agcgggagaa cgcgtcctcg cccgccggcc gggaggcccc ggagctggcc catggggagc  1380
aggcgcccgg tgccggccac gacgaccgcc accgccgcg ccgcgaccgg ccggtgaagc  1440
ccagggaccc ccctctggga gagcccatg agggcaggag agtgatggag agtacgccca  1500
gcttcctgaa gggcacccca acctgggaga agacggcccc agagaacggc atcgtgagac  1560
aggagcccgg cagccgcct cgagatggac tgcaccatgg ccgctgtgc ctgggagagc  1620
ctgctccctt ttggagggc gtcctgagca cccagactc ctggcttccc cctggcttcc  1680
cccagggccc caaggacatg ctcccacttg tggagggcga gggccccag aatggggaga  1740
ggaaggtcaa ctggctgggc agcaaagagg gactgcgctg gaaggaggcc atgcttaccc  1800
atccgctggc attctgcggg ccagcgtgcc cacctcgctg tggccccctg atgcctgagc  1860
atagtggtgg ccatctcaag agtgacctg tggccttccg gccctggcac tgcccttttcc  1920
```

FIGURE 1B

```
ttctggagac caagatcctg gagcgagctc ccttctgggt gcccacctgc ttgccaccct   1980
acctagtgtc tggcctgccc ccagagcatc catgtgactg cccctgacc ccgcacccct    2040
gggtatactc cggggggccag cccaaagtgc cctctgcctt cagcttaggc agcaagggct  2100
tttactacaa ggatccgagc attcccaggt tggcaaagga gcccttggca gctgcggaac  2160
ctgggttgtt tggcttaaac tctggtgggc acctgcagag agccggggag gccgaacgcc  2220
cttcactgca ccagagggat ggagagatgg gagctggccg gcagcagaat ccttgcccgc  2280
tcttcctggg gcagccagac actgtgccct ggacctcctg gcccgcttgt ccccaggcc    2340
ttgttcatac tcttggcaac gtctgggctg ggccaggcga tgggaacctt gggtaccagc  2400
tggggccacc agcaacacca aggtgcccct ctcctgagcc gcctgtcacc cagcggggct  2460
gctgttcatc ctacccaccc actaaaggtg gggatcttgg cccttgtggg aagtgccagg  2520
agggcctgga gggggtgcc agtggagcca gcgaacccag cgaggaagtg aacaaggcct    2580
ctggccccag ggcctgtccc ccagccacc acaccaagct gaagaagaca tggctcacac    2640
ggcactcgga gcagtttgaa tgtccacgcg gctgcctga ggtcgaggag aggccggttg    2700
ctcggctccg ggccctcaaa agggcaggca gccccgaggt ccagggagca atgggcagtc  2760
cagcccccaa gcggccaccg gaccctttcc caggcactgc agaacagggg gctgggggtt  2820
ggcaggaggt gcgggacaca tcgataggga acaaggatgt ggactcggga cagcatgatg  2880
agcagaaagg accccaagat ggccaggcca gtctccagga cccgggactt caggacatac  2940
catgcctggc tctccctgca aaactggctc aatgccaaag ttgtgcccag gcagctggag  3000
agggaggagg gcacgcctgc cactctcagc aagtgcggag atcgcctctg ggaggggagc  3060
tgcagcagga ggaagacaca gccaccaact ccagctctga ggaaggccca gggtccggcc  3120
ctgacagccg gctcagcaca ggcctcgcca agcacctgct cagtggtttg ggggaccgac  3180
tgtgccgcct gctgcggagg gagcgggagg ccctggcttg ggcccagcgg gaaggccaag  3240
ggccagccgt gacagaggac agcccaggca ttccacgctg ctgcagccgt tgccaccatg  3300
gactcttcaa caccccactgg cgatgtcccc gctgcagcca ccggctgtgt gtggcctgtg  3360
gtcgtgtggc aggcactggg cgggccaggg agaaagcagg ctttcaggag cagtccgcgg  3420
aggagtgcac gcaggaggcc gggcacgctg cctgttccct gatgctgacc cagtttgtct  3480
ccagccaggc tttggcagag ctgagcactg caatgcacca ggtctgggtc aagtttgata  3540
tccgggggca ctgcccctgc caagctgatg cccgggtatg ggccccgggg gatgcaggcc  3600
agcagaagga atcaacacag aaaacgcccc caactccaca accttcctgc aatggcgaca  3660
cccacaggac caagagcatc aaagaggaga ccccgattc cgctgagacc ccagcagagg  3720
accgtgctgg ccgagggccc ctgccttgtc cttctctctg cgaactgctg gcttctaccg  3780
cggtcaaact ctgcttgggc catgagcgaa tacacatggc cttcgccccc gtcactccgg  3840
```

FIGURE 1C

```
ccctgcccag tgatgaccgc atcaccaaca tcctggacag cattatcgca caggtggtgg    3900
aacggaagat ccaggagaaa gccctggggc cggggcttcg agctggcccg ggtctgcgca    3960
agggcctggg cctgcccctc tctccagtgc ggccccggct gcctccccca ggggctttgc    4020
tgtggctgca ggagcccag ccttgccctc ggcgtggctt ccacctcttc caggagcact     4080
ggaggcaggg ccagcctgtg ttggtgtcag ggatccaaag gacattgcag gcaacctgt     4140
gggggacaga agctcttggg gcacttggag gccaggtgca ggcgctgagc ccctcggac     4200
ctccccagcc cagcagcctg ggcagcacaa cattctggga gggcttctcc tggcctgagc    4260
ttcgcccaaa gtcagacgag ggctctgtcc tcctgctgca ccgagctttg ggggatgagg    4320
acaccagcag ggtggagaac ctagctgcca gtctgccact tccggagtac tgcgccctcc    4380
atggaaaact caacctggct tcctacctcc caccgggcct tgccctgcgt ccactggagc    4440
cccagctctg ggcagcctat ggtgtgagcc cgcaccgggg acacctgggg accaagaacc    4500
tctgtgtgga ggtggccgac ctggtcagca tcctggtgca tgccgacaca ccactgcctg    4560
cctggcaccg ggcacagaaa gacttccttt caggcctgga cggggagggg ctctggtctc    4620
cgggcagcca ggtcagcact gtgtggcacg tgttccgggc acaggacgcc cagcgcatcc    4680
gccgctttct ccagatggtg tgcccggccg gggcaggcgc cctggagcct ggcgccccag    4740
gcagctgcta cctggatgca gggctgcggc ggcgcctgcg ggaggagtgg ggcgtgagct    4800
gctggaccct gctccaggcc cccggagagg ccgtgctggt gcctgcaggg gctccccacc    4860
aggtgcaggg cctggtgagc acagtcagcg tcactcagca cttcctctcc cctgagacct    4920
ctgccctctc tgctcagctc tgccaccagg gacccagcct tccccctgac tgccacctgc    4980
tttatgccca gatggactgg gctgtgttcc aagcagtgaa ggtggccgtg gggacattac    5040
aggaggccaa atagagggat gctaggtgtc tgggatcggg gtggggacag gtagaccagg    5100
tgctcagccc aggcacaact tcagcagggg atggcgctag gggacttggg gatttctggt    5160
caaccccaca agcaccactc tgggcacaag caggcactc tgttcccctc cccttaagc     5220
caacaaccac agtgccacca agctcacacc tgtccttctc aggctggcat ctcccccacc    5280
ctgtgcccct tttcatggta ccaggccgc actgggggca attgacttcc tccaatcccc     5340
actcctccga gacccaggag acaaacagcc cttccttggg gaaacttggg aatcattctg    5400
gcttaaacaa cacctcctcc tgctgctcac tccgctgag ccactctac tgccccagct     5460
ccgtttctac caccgcatcc tcactgggct cactgcaggc atgctgaaca ggggcctcc    5520
aaccttctgc cctcctgcca aagatctgg ggagtgtgag gagagggtgg catcaggagc     5580
tgctcaggct tggcggaggg agcggcatgg gcgatgtcac tcatgccctt cccggtccgc    5640
ccgcttccct ccttcatgat ttccattaaa gtctgttgtt ttgaaaaaaa aaaaaaaaa     5700
aaaaaaaa                                                              5709
```

NUCLEIC ACIDS FOR INHIBITING HAIRLESS PROTEIN EXPRESSION AND METHODS OF USE THEREOF

CROSS-REFERENCE TO RELATED APPLICATIONS

This application is a divisional of U.S. patent application Ser. No. 12/139,818 filed Jun. 16, 2008, now abandoned, which is a continuation of U.S. patent application Ser. No. 10/122,013 filed Apr. 12, 2002, which issued as U.S. Pat. No. 7,423,022 on Sep. 9, 2008, which claims the benefit of priority of U.S. Provisional Application No. 60/283,618 filed Apr. 13, 2001, the contents of each of which are hereby incorporated by reference in their entirety.

BACKGROUND OF THE INVENTION

The Hairless Gene

The hairless mouse, a frequent subject of different dermatological experiments, is characterized by hair loss that starts at the age of 14 days postpartum from the upper eyelids and progresses caudally. The process is completed by the age of 3 weeks, when the mice are entirely naked and never grow hair again (Panteleyev et al. 1998b). The phenotype results from proviral integration and consequential aberrant splicing in the mouse hairless gene. Lack of expression of the mouse hairless gene due to inherited mutations leads to the complete loss of hair, known as atrichia. Other mutations have been identified in other mouse hairless alleles, and its human equivalent, resulting in essentially similar phenotypes (Ahmad et al. 1998a; Ahmad et al. 1998b; Panteleyev et al. 1998a). Those studies demonstrated that hairless expression in the hair follicle is necessary for hair cycling, specifically in the transition to the catagen phase.

Catalytic Nucleic Acid Molecules

Gene therapy is perhaps the most exciting promise of modern medical science. The technology of replacing mutant genes with correct ones can provide definitive therapy for a number of diseases. There are, however, conditions—inherited and acquired alike—which cannot be treated by the introduction of a new gene. In many cases, the ablation of an already existing gene may be desirable. In many dominantly inherited diseases, the successful "knock-out" of the mutant gene is, in theory, sufficient to cure the disease. In some other cases, the elimination of a normally functioning, wild-type gene may be necessary for therapeutic gene targeting.

Such is the case in abundant hair growth or hirsutism, in which inhibiting genes which promote hair growth could lead to decreased hair growth and, therefore, improvement. One way to achieve targeted, transient gene suppression is likely going to be through the use of catalytic nucleic acid technology, which includes both ribozymes and DNAzymes.

Ribozymes are RNA structures having a self-catalytic enzymatic function which, together with their sequence-specific and RNA-binding ability, make them capable of cleaving other RNA molecules at specific target sequences (Cech 1987). Recent success has been achieved in engineering ribozymes capable of selectively recognizing target sequences carrying different types of mutations, including single base-pair missense mutations (Parthasarathy et al. 1999; Sioud and Drlica 1991; Vaish et al. 1998).

These encouraging achievements give new perspective to experimental strategies using selective mRNA ablation (Phylactou et al. 1998). The different groups of ribozymes described thus far (including hairpin ribozymes, hammerhead ribozymes and group I intron ribozymes (Bartel 1999)) have different characteristics with respect to their mechanism of splicing, splicing efficiency and target specificity. Several studies have used hammerhead ribozymes to selectively cleave RNA because of the superior target specificity of these ribozymes (Long and Sullenger 1999; Phylactou et al. 1998; Vaish et al. 1998).

Ribozymes can be delivered exogenously, such that the ribozymes are synthesized in vitro. They are usually administered using carrier molecules (Sioud 1996) or without carriers, using ribozymes specially modified to be nuclease-resistant (Flory et al. 1996). The other method is endogenous delivery, in which the ribozymes are inserted into a vector (usually a retroviral vector) which is then used to transfect target cells. There are several possible cassette constructs to chose from (Vaish et al. 1998), including the widely used U1 snRNA expression cassette, which proved to be efficient in nuclear expression of hammerhead ribozymes in various experiments (Bertrand et al. 1997; Michienzi et al. 1996; Montgomery and Dietz 1997).

Recent efforts have led to the successful development of small DNA oligonucleotides that have a structure similar to the hammerhead ribozyme (Santoro and Joyce 1997). These molecules are known as "deoxy-ribozymes", "deoxyribozymes" and "DNAzymes", and are virtually DNA equivalents of the hammerhead ribozymes. They consist of a 15 bp catalytic core and two sequence-specific arms with a typical length of 5-13 bp each (Santoro and Joyce 1998). Deoxyribozymes have more lenient consensus cleavage site requirements than hammerhead ribozymes, and are less likely to degrade when used for in vivo applications. The most widely used type of these novel catalytic molecules is known as the "10-23" deoxy-ribozyme, whose designation originates from the numbering used by its developers (Santoro and Joyce 1997). Because of their considerable advantages, deoxy-ribozymes have already been used in a wide spectrum of in vitro and in vivo applications (Cairns et al. 2000; Santiago et al. 1999).

SUMMARY OF THE INVENTION

This invention provides a catalytic deoxyribonucleic acid molecule that specifically cleaves Hairless Protein mRNA comprising:

(a) a catalytic domain that cleaves mRNA at a defined consensus sequence;

(b) a binding domain contiguous with the 5' end of the catalytic domain; and (c) a binding domain contiguous with the 3' end of the catalytic domain, wherein the binding domains are complementary to, and therefore hybridize with, the two regions flanking the defined consensus sequence within the Hairless Protein mRNA at which cleavage is desired, and wherein each binding domain is at least 4 residues in length, and both binding domains have a combined total length of at least 8 residues.

This invention also provides a catalytic ribonucleic acid molecule that specifically cleaves Hairless Protein mRNA comprising:

(a) a catalytic domain that cleaves mRNA at a defined consensus sequence;

(b) a binding domain contiguous with the 5' end of the catalytic domain; and (c) a binding domain contiguous with the 3' end of the catalytic domain, wherein the binding domains are complementary to, and therefore hybridize with, the two regions flanking the defined consensus sequence within the Hairless Protein mRNA at which cleavage is desired, and wherein each binding domain is at least 4 residues in length, and both binding domains have a combined total length of at least 8 residues.

This invention also provides a first pharmaceutical composition comprising the instant catalytic ribonucleic acid molecule or deoxyribonucleic acid molecule and a pharmaceutically acceptable carrier.

This invention further provides a method of specifically cleaving Hairless Protein mRNA comprising contacting the mRNA with either of the instant catalytic nucleic acid molecules under conditions permitting the molecule to cleave the mRNA.

This invention further provides a method of specifically cleaving Hairless Protein mRNA in a cell, comprising contacting the cell containing the mRNA with either of the instant catalytic nucleic acid molecules so as to specifically cleave the hairless protein mRNA in the cell.

This invention further provides a method of specifically inhibiting the expression of Hairless Protein in a cell that would otherwise express Hairless Protein, comprising contacting the cell with either of the instant catalytic nucleic acid molecules so as to specifically inhibit the expression of Hairless Protein in the cell.

This invention further provides a method of specifically inhibiting the expression of Hairless Protein in a subject's cells comprising administering to the subject an amount of either of the instant catalytic nucleic acid molecules effective to specifically inhibit the expression of Hairless Protein in the subject's cells.

This invention further provides a method of specifically inhibiting the expression of Hairless Protein in a subject's cells comprising administering to the subject an amount of the first pharmaceutical composition effective to specifically inhibit the expression of Hairless Protein in the subject's cells.

This invention further provides a method of inhibiting hair production by a hair-producing cell comprising contacting the cell with an effective amount of either of the instant catalytic nucleic acid molecules.

This invention further provides a method of inhibiting hair growth in a subject comprising administering to the subject an effective amount of the first pharmaceutical composition.

This invention further provides a method of inhibiting the transition of a hair follicle from the anagen phase to the catagen phase comprising contacting the follicle with an effective amount of either of the instant catalytic nucleic acid molecules or the first pharmaceutical composition.

This invention further provides a vector which comprises a sequence encoding either of the instant catalytic nucleic acid molecules.

This invention further provides a host-vector system comprising a cell having the instant vector therein. This invention still further provides a method of producing either of the instant catalytic nucleic acid molecules comprising culturing a cell having therein a vector comprising a sequence encoding either catalytic nucleic acid molecule under conditions permitting the expression of the catalytic nucleic acid molecule by the cell.

This invention further provides a nucleic acid molecule that specifically hybridizes to Hairless Protein mRNA so as to inhibit the translation thereof in a cell.

The invention further provides a second pharmaceutical composition comprising (a) the instant nucleic acid molecule or the instant vector and (b) a pharmaceutically acceptable carrier.

This invention further provides a method of specifically inhibiting the expression of Hairless Protein in a cell that would otherwise express Hairless Protein, comprising contacting the cell with the instant nucleic acid molecule so as to specifically inhibit the expression of Hairless Protein in the cell.

This invention further provides a method of specifically inhibiting the expression of Hairless Protein in a subject's cells comprising administering to the subject an amount of the instant nucleic acid molecule effective to specifically inhibit the expression of Hairless Protein in the subject's cells.

This invention further provides a method of specifically inhibiting the expression of Hairless Protein in a subject's cells comprising administering to the subject an amount of the second pharmaceutical composition effective to specifically inhibit the expression of Hairless Protein in the subject's cells.

This invention further provides a method of inhibiting hair production by a hair-producing cell comprising contacting the cell with an effective amount of the instant nucleic acid molecule.

This invention further provides a method of inhibiting hair growth in a subject comprising administering to the subject an effective amount of the second pharmaceutical composition.

This invention further provides a method of inhibiting the transition of a hair follicle from the anagen phase to the catagen phase comprising contacting the follicle with an effective amount of the instant nucleic acid molecule or the second pharmaceutical composition.

This invention further provides a method of producing the instant nucleic acid molecule comprising culturing a cell having therein a vector comprising a sequence encoding said nucleic acid molecule under conditions permitting the expression of the nucleic acid molecule by the cell.

Finally this invention provides a non-human transgenic mammal, wherein the mammal's genome:
(a) has stably integrated therein a nucleotide sequence encoding a human Hairless Protein operably linked to a promoter, whereby the nucleotide sequence is expressed; and
(b) lacks an expressible endogenous hairless Protein-encoding nucleic acid sequence.

BRIEF DESCRIPTION OF THE FIGURES

FIGS. 1A-1C: These figures show the mRNA sequence of Human Hairless Protein (SEQ ID NO:1).

FIGS. 2B-2D show the pathology of C67BL/J mice treated with anti-Hairless Protein deoxyribozymes. FIG. 2A shows a control area treated with a non-specific deoxyribozyme.

Figure 2B:
FIGS. 2A-2D.
Figure 2D:
Figure 2A:
Figure 2C:
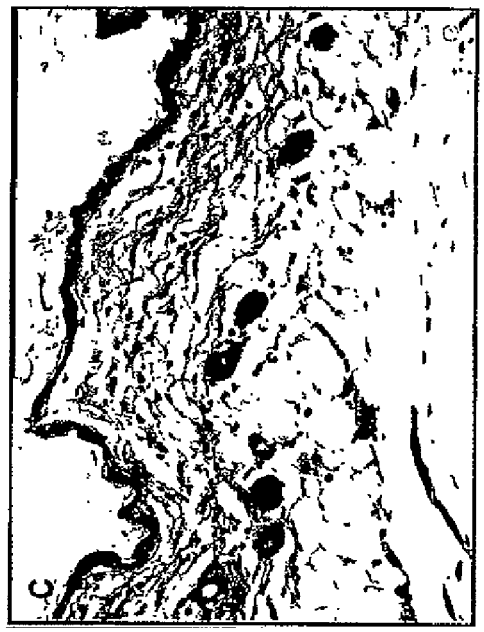

(SEQ ID NO:26) and ODN2 (SEQ ID NO:27), respectively, were added to the medium at 40 μM concentration prior to transfection.

DETAILED DESCRIPTION OF THE INVENTION

Definitions

As used herein, and unless stated otherwise, each of the following terms shall have the definition set forth below.

"Administering" shall mean administering according to any of the various methods and delivery systems known to those skilled in the art. The administering can be performed, for example, via implant, transmucosally, transdermally and subcutaneously. In the preferred embodiment, the administering is topical and preferably dermal.

"Catalytic" shall mean the functioning of an agent as a catalyst, i.e. an agent that increases the rate of a chemical reaction without itself undergoing a permanent structural change.

"Consensus sequence" shall mean a nucleotide sequence of at least two residues in length between which catalytic nucleic acid cleavage occurs. For example, consensus sequences include "A:C" and "G:U".

"Hairless Protein" shall mean the protein encoded by the nucleotide sequence shown in FIGS. 1A-1C (SEQ ID NO:1) and having the amino acid sequence shown in SEQ ID NO:17, and any variants thereof, whether artificial or naturally occurring. Variants include, without limitation, homologues, post-translational modifications, mutants such as those commonly referred to as T1022A, 1256delC, 1261del21, R620Q, 2001delCCAG, 2776+1G→A, N970K V1136D, 3434delC and 2147delC, and polymorphisms such as the one commonly referred to as L526P.

"Hairless Protein mRNA" shall mean any mRNA molecule comprising a sequence which encodes Hairless Protein. Hairless Protein mRNA includes, without limitation, protein-encoding sequences as well as the 5' and 3' non-protein-encoding sequences. An example of Hairless Protein mRNA is the mRNA sequence shown in FIG. 1. As used herein, the terms "Hairless Protein", "Hairless", "hairless protein" and "hairless" are used interchangeably, unless stated otherwise.

"Hybridize" shall mean the annealing of one single-stranded nucleic acid molecule to another nucleic acid molecule based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook, 1989).

"Inhibit" shall mean to slow, stop or otherwise impede.

"Nucleic acid molecule" shall mean any nucleic acid molecule, including, without limitation, DNA, RNA and hybrids thereof The nucleic acid bases that form nucleic acid molecules can be the bases A, C, G, T and U, as well as derivatives thereof Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Pharmaceutically acceptable carrier" shall mean any of the various carriers known to those skilled in the art. In one embodiment, the carrier is an alcohol, preferably ethylene glycol. In another embodiment, the carrier is a liposome. The following pharmaceutically acceptable carriers are set forth, in relation to their most commonly associated delivery systems, by way of example, noting the fact that the instant pharmaceutical compositions are preferably delivered dermally.

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in this invention include the following: (1) CellFectin, 1:1.5 (M/M) liposome formulation of the cationic lipid N,NI,NII,NIII-tetramethyl-N,NI,NII,NIII-tetrapalmity-spermine and dioleoyl phosphatidylethanol-amine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniummethylsulfate) (Boehringer Manheim); and (4) Lipofectamine, 3:1 (M/M) liposome formulation of the polycationic lipid DOSPA and the neutral lipid DOPE (GIBCO BRL).

Transmucosal delivery systems include patches, tablets, suppositories, pessaries, gels and creams, and can contain excipients such as solubilizers, and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

"Specifically cleave", when referring to the action of one of the instant catalytic nucleic acid molecules on a target mRNA molecule, shall mean to cleave the target mRNA molecule without cleaving another mRNA molecule lacking a sequence complementary to either of the catalytic nucleic acid molecule's two binding domains.

"Subject" shall mean any animal, such as a human, a primate, a mouse, a rat, a guinea pig or a rabbit.

"Vector" shall include, without limitation, a nucleic acid molecule that can be used to stably introduce a specific nucleic acid sequence into the genome of an organism.

Finally, the following abbreviations shall have the meanings set forth below: "A" shall mean Adenine; "bp" shall mean base pairs; "C" shall mean Cytosine; "DNA" shall mean deoxyribonucleic acid; "G" shall mean Guanine; "mRNA" shall mean messenger ribonucleic acid; "RNA" shall mean ribonucleic acid; "RT-PCR" shall mean reverse transcriptase polymerase chain reaction; "RY" shall mean purine:pyrimidine; "T" shall mean Thymine; and "U" shall mean Uracil.

Embodiments of the Invention

This invention provides a catalytic deoxyribonucleic acid molecule that specifically cleaves Hairless Protein mRNA comprising:

(a) a catalytic domain that cleaves mRNA at a defined consensus sequence;

(b) a binding domain contiguous with the 5' end of the catalytic domain; and (c) a binding domain contiguous with the 3' end of the catalytic domain, wherein the binding domains are complementary to, and therefore hybridize with, the two regions flanking the defined consensus sequence within the Hairless Protein mRNA at which cleavage is desired, and wherein each binding domain is at least 4 residues in length, and both binding domains have a combined total length of at least 8 residues. In the preferred embodiment, each binding domain is 7 residues in length, and both binding domains have a combined total length of 14 residues.

The catalytic domain may optionally contain stem-loop structures in addition to the nucleotides required for catalytic activity. In one embodiment of the instant catalytic deoxyribonucleic acid molecule, the catalytic domain has the sequence ggctagctacaacga (SEQ ID NO:18), and cleaves mRNA at the consensus sequence purine:pyrimidine. In a preferred embodiment, cleavage occurs at one or more of the following cleavage sites in the Hairless Protein mRNA (shown in FIGS. 1A-1C and SEQ ID NO:1), wherein the indicated nucleotide residue immediately precedes the cleavage site: 1594, 1597, 1641, 1698, 1732, 1750, 1801, 1811, 2028, 2033, 2047, 2083, 2269, 2380 and 2395.

In another embodiment the instant deoxyribonucleic acid molecule has a sequence selected from the group consisting of:

```
(a) cccatggggctagctacaacgagcagtcc;   (SEQ ID NO: 2)

(b) cggcccaggctagctacaacgaggtgcag;   (SEQ ID NO: 3)

(c) ctcaggaggctagctacaacgagcccctc;   (SEQ ID NO: 4)

(d) gggagcaggctagctacaacgagtccttg;   (SEQ ID NO: 5)

(e) ctccccaggctagctacaacgatctgggg;   (SEQ ID NO: 6)

(f) cagccagggctagctacaacgatgacctt;   (SEQ ID NO: 7)

(g) cagcggaggctagctacaacgagggtaag;   (SEQ ID NO: 8)

(h) cgcagaaggctagctacaacgagccagcg;   (SEQ ID NO: 9)

(i) tgcgggggggctagctacaacgacaggggc;  (SEQ ID NO: 10)

(j) aggggtgggctagctacaacgaggggtca;   (SEQ ID NO: 11)

(k) cccggagggctagctacaacgaataccca;   (SEQ ID NO: 12)

(l) gcctaagggctagctacaacgatgaaggc;   (SEQ ID NO: 13)
```

-continued
```
(m) gcaaggaggctagctacaacgatctgctg;   (SEQ ID NO: 14)

(n) gttcccaggctagctacaacgacgcctgg;   (SEQ ID NO: 15)
and (o) cagctggggctagctacaacgaacccaag.   (SEQ ID NO: 16)
```

This invention also provides a catalytic ribonucleic acid molecule that specifically cleaves Hairless Protein mRNA comprising:

(a) a catalytic domain that cleaves mRNA at a defined consensus sequence;

(b) a binding domain contiguous with the 5' end of the catalytic domain; and (c) a binding domain contiguous with the 3' end of the catalytic domain, wherein the binding domains are complementary to, and therefore hybridize with, the two regions flanking the defined consensus sequence within the Hairless Protein mRNA at which cleavage is desired, and wherein each binding domain is at least 4 residues in length and both binding domains have a combined total length of at least 8 residues.

In one embodiment of the instant catalytic ribonucleic acid molecule, each binding domain is at least 12 residues in length. In the preferred embodiment, each binding domain is no more than 17 residues in length. In another embodiment, both binding domains have a combined total length of at least 24 residues, and no more than 34 residues.

Preferably, the instant catalytic ribonucleic acid molecule is a hammerhead ribozyme. Hammerhead ribozymes are well known in the literature, as described in Pley et al, 1994. In one embodiment, the consensus sequence is the sequence 5'-NUH-3', where N is any nucleotide, U is uridine and H is any nucleotide except guanine. An example of such sequence is 5'-adenine:uracil:adenine-3'. In another embodiment, the catalytic domain has the sequence ctgatgagtccgtgaggacgaaaca (SEQ ID NO:19).

In this invention, the instant catalytic nucleic acid molecules can cleave Hairless Protein mRNA at each and any of the consensus sequences therein. Since ribozyme and DNAzyme consensus sequences are known, and the Hairless Protein mRNA sequence is known, one of ordinary skill could readily construct a catalytic nucleic acid molecule directed to any of the Hairless Protein mRNA consensus sequences based on the instant specification. In a preferred embodiment, the cleavage occurs at one or more of the following cleavage sites in Hairless Protein mRNA (sequence shown in FIGS. 1A-1C and SEQ ID NO:1), wherein the indicated nucleotide residue immediately precedes the cleavage site: −94, 159, 264, 506, 847 and 879. The number −94 indicates a target site upstream from the 5' end of the sequence shown in FIG. 1, in the 5' untranslated region of the sequence.

In another embodiment, the instant catalytic ribonucleic acid molecule has a sequence selected from the group consisting of:

```
(a) cggccggcgggcgagctgatgagtccgtgaggacgaaacacgcgttctcccgctct;        (SEQ ID NO: 20)

(b) gagtctggggtgctcagctgatgagtccgtgaggacgaaacacgcccctccaaaaagg;      (SEQ ID NO: 21)

(c) ttgctgcccagccagttctgatgagtccgtgaggacgaaacaccttcctctccccatt;      (SEQ ID NO: 22)

(d) gctctgggggcaggccactgatgagtccgtgaggacgaaacacactaggtagggtggc;      (SEQ ID NO: 23)

(e) atgaacaaggctggggctgatgagtccgtgaggacgaaacacaagcgggccaggagg;       (SEQ ID NO: 24)
and (f) tcgcctggcccagcccactgatgagtccgtgaggacgaaacacgttgccaagagtatg.      (SEQ ID NO: 25)
```

In an alternative embodiment of the instant catalytic ribonucleic acid molecule, the molecule is a hairpin ribozyme. Hairpin ribozymes are well known in the literature as described in Fedor (2000).

Catalytic nucleic acid molecules can be directed to any cleavage site within the Hairless Protein mRNA, preferably within the 5' half of the mRNA. In one embodiment the cleavage site within the hairless protein mRNA is located within the first 3000 residues following the mRNA's 5' terminus. In another embodiment cleavage occurs within the first 1500 residues. Here, "following" means in the 3' direction of the 5' terminus.

The Hairless Protein mRNA cleaved by the instant catalytic nucleic acid molecules can be from any subject. In one embodiment, the Hairless Protein mRNA is from a subject selected from the group consisting of human, monkey, rat and mouse, and in the preferred embodiment is human. In the preferred embodiment, the Hairless Protein mRNA has the sequence shown in FIGS. 1A-1C.

This invention also provides a first pharmaceutical composition comprising the instant catalytic ribonucleic acid molecule or deoxyribonucleic acid molecule and a pharmaceutically acceptable carrier.

This invention further provides a method of specifically cleaving Hairless Protein mRNA comprising contacting the mRNA with either of the instant catalytic nucleic acid molecules under conditions permitting the molecule to cleave the mRNA. These conditions are well known in the art and include physiological conditions.

This invention further provides a method of specifically cleaving Hairless Protein mRNA in a cell, comprising contacting the cell containing the mRNA with either of the instant catalytic nucleic acid molecules so as to specifically cleave the hairless protein mRNA in the cell. The cell containing Hairless Protein mRNA can be, for example, a naturally occurring cell or a transgenic cell. In the preferred embodiment, the cell is a keratinocyte.

This invention further provides a method of specifically inhibiting the expression of Hairless Protein in a cell that would otherwise express Hairless Protein, comprising contacting the cell with either of the instant catalytic nucleic acid molecules so as to specifically inhibit the expression of Hairless Protein in the cell.

This invention further provides a method of specifically inhibiting the expression of Hairless Protein in a subject's cells comprising administering to the subject an amount of either of the instant catalytic nucleic acid molecules effective to specifically inhibit the expression of Hairless Protein in the subject's cells.

This invention further provides a method of specifically inhibiting the expression of Hairless Protein in a subject's cells comprising administering to the subject an amount of the first pharmaceutical composition effective to specifically inhibit the expression of Hairless Protein in the subject's cells.

Determining the effective amount of the instant pharmaceutical composition can be done based on animal data using routine computational methods. In one embodiment, the effective amount contains between about 10 ng and about 100 µg of the instant nucleic acid molecules per square centimeter of skin. In another embodiment, the effective amount contains between about 100 ng and about 10 µg of the nucleic acid molecules per square centimeter of skin. In a further embodiment, the effective amount contains between about 1 µg and about 5 µg and preferably about 2 µg, of the nucleic acid molecules per square centimeter of skin.

This invention further provides a method of inhibiting hair production by a hair-producing cell comprising contacting the cell with an effective amount of either of the instant catalytic nucleic acid molecules.

This invention further provides a method of inhibiting hair growth in a subject comprising administering to the subject an effective amount of the first pharmaceutical composition.

Hair follicles are dynamic structures that generate hair through a regulated cycle of growth and remodeling. The hair follicle cycles between rest (telogen), I growth (anagen) and regression (catagen). This invention further provides a method of inhibiting the transition of a hair follicle from the anagen phase to the catagen phase comprising contacting the follicle with an effective amount of either of the instant catalytic nucleic acid molecules or the first pharmaceutical composition.

This invention further provides a vector which comprises a sequence encoding either of the instant catalytic nucleic acid molecules.

This invention further provides a host-vector system comprising a cell having the instant vector therein. This invention still further provides a method of producing either of the instant catalytic nucleic acid molecules comprising culturing a cell having therein a vector comprising a sequence encoding either catalytic nucleic acid molecule under conditions permitting the expression of the catalytic nucleic acid molecule by the cell. Methods of culturing cells in order to permit expression and conditions permitting expression are well known in the art. For example see Sambrook et al. (1989). Such methods can optionally comprise a further step of recovering the nucleic acid product.

This invention provides a nucleic acid molecule that specifically hybridizes to Hairless Protein mRNA so as to inhibit the translation thereof in a cell.

In one embodiment, the instant nucleic acid is a ribonucleic acid. In another embodiment the nucleic acid is deoxyribonucleic acid.

The invention further provides a second pharmaceutical composition comprising (a) the instant nucleic acid molecule or the instant vector and (b) a pharmaceutically accpetable carrier.

This invention further provides a method of specifically inhibiting the expression of Hairless Protein in a cell that would otherwise express Hairless Protein, comprising contacting the cell with the instant nucleic acid molecule so as to specifically inhibit the expression of Hairless Protein in the cell.

This invention further provides a method of specifically inhibiting the expression of Hairless Protein in a subject's cells comprising administering to the subject an amount of the instant nucleic acid molecule effective to specifically inhibit the expression of Hairless Protein in the subject's cells.

This invention further provides a method of specifically inhibiting the expression of Hairless Protein in a subject's cells comprising administering to the subject an amount of the second pharmaceutical composition effective to specifically inhibit the expression of Hairless Protein in the subject's cells.

This invention further provides a method of inhibiting hair production by a hair-producing cell comprising contacting the cell with an effective amount of the instant nucleic acid molecule.

This invention further provides a method of inhibiting hair growth in a subject comprising administering to the subject an effective amount of the second pharmaceutical composition.

This invention further provides a method of inhibiting the transition of a hair follicle from the anagen phase to the catagen phase comprising contacting the follicle with an effective amount of the instant nucleic acid molecule or the second pharmaceutical composition.

This invention further provides a method of producing the instant nucleic acid molecule comprising culturing a cell having therein a vector comprising a sequence encoding said nucleic acid molecule under conditions permitting the expression of the nucleic acid molecule by the cell.

Finally this invention provides a non-human transgenic mammal, wherein the mammal's genome:
(a) has stably integrated therein a nucleotide sequence encoding a human Hairless Protein operably linked to a promoter, whereby the nucleotide sequence is expressed; and
(b) lacks an expressible endogenous Hairless Protein-encoding nucleic acid sequence.

In the preferred embodiment, the transgenic mammal is a mouse. The instant transgenic mammal is useful as a model for testing hair removal products which function by inhibiting Hairless Protein expression.

In this invention, the various embodiments of subjects, pharmaceutically acceptable carriers, dosages, cell types, routes of administration and target nucleic acid sequences are envisioned for each of the instant nucleic acid molecules, pharmaceutical compositions and methods. Moreover, in this invention, the various embodiments of methods, subjects, pharmaceutically acceptable carriers, dosages, cell types, routes of administration and target nucleic acid sequences are envisioned for all non-nucleic acid agents which inhibit the expression of Hairless Protein. Such non-nucleic acid agents include, without limitation, polypeptides, carbohydrates and small organic compounds.

This invention will be better understood by reference to the Experimental Details which follow, but those skilled in the art will readily appreciate that the specific experiments detailed are only illustrative of the invention as described more fully in the claims which follow thereafter.

Experimental Details

Part I—Catalytic Nucleic Acids
Introduction

Catalytic nucleic acid technology is widely used to target mRNA in a sequence-specific fashion, and thus change the expression pattern of cells or tissues. While the goal of mRNA targeting is usually the cleavage of mutant mRNA with the prospect of gene therapy for inherited diseases, in certain instances targeting of wild-type genes can be used therapeutically.

Lack of expression of the mouse hairless gene due to inherited mutations leads to the complete loss of hair, known as atrichia. This study was designed to recapitulate the hairless phenotype in a restricted manner by topical application of deoxy-ribozyme molecules to specifically cleave the mouse hairless mRNA. Pathology samples taken from the treated area at different times demonstrated a decreased number of hair follicles, involution of the remaining follicles, separation of the dermal papillae and the presence of dermal cysts, all characteristics of the hairless phenotype but not normally present in the skin of C57B1/6J mice.

In this study, the hairless phenotype is successfully recapitulated using topically applied target-specific catalytic oligonucleotides designed to cleave the mouse hairless mRNA. Hence, this invention demonstrates the feasibility of using ribozyme and deoxy-ribozyme technology to alter gene expression in the skin via topical application and provide permanent hair removal.

Materials and Methods

Figure 3:
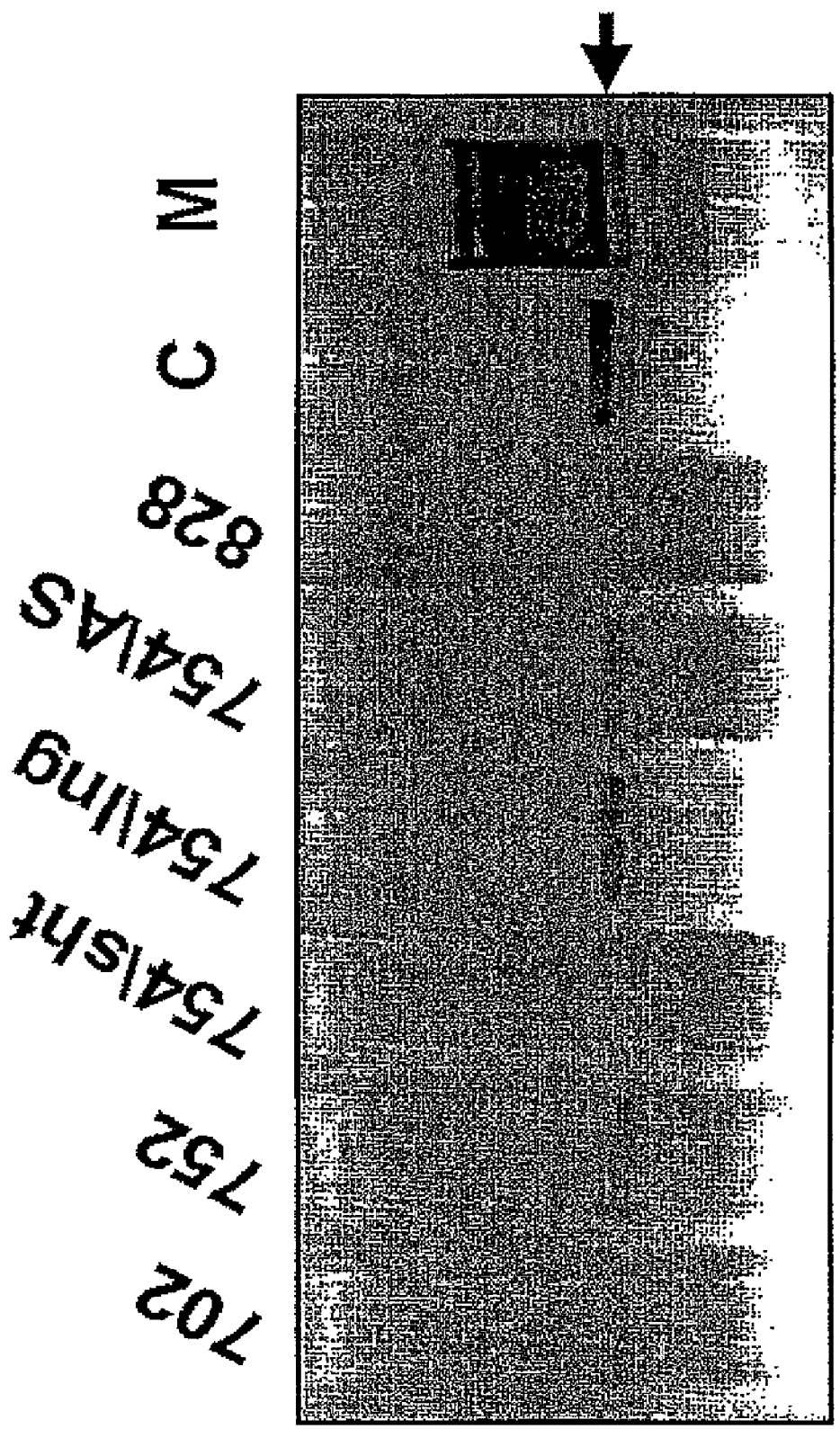
FIG. 3: This figure shows reverse transcriptase polymerase chain reaction products visualized on an ethidium bromide-containing 2% agarose gel under UV light. Those deoxyribozymes that were capable of cleaving the target mouse Hairless Protein mRNA with the highest efficiency were used for in vivo experiments, as shown in lanes ("702") and 3 ("754\sht").

Deoxy-ribozyme design and in vitro testing. To target the mouse hairless mRNA, a series of deoxy-ribozymes were designed based on the consensus cleavage sites 5'-RY-3' in the mRNA sequence (GenBank Accession#: AF039196) (Ahmad et al. 1998a). Only those potential cleavage sites which were located on an open loop of the mRNA according to the RNA folding software RNADRaw 2.1 were targeted (Matzura and Wennborg 1996). The deoxy-ribozyme design utilized the previously described structure (Santoro and Joyce 1997; Santoro and Joyce 1998) where two sequence-specific arms were attached to a catalytic core based on the mouse hairless mRNA sequence. The deoxy-ribozymes were custom synthesized (Life Technologies). Commercially available mouse brain polyA-RNA (Ambion) served as a template in the in vitro cleavage reaction to test the efficiency of the deoxy-ribozymes. 800 ng RNA template were incubated in the presence of 20 mM Mg2++ and RNAse Out RNAse inhibitor (Life Technologies) at pH 7.5 with 2 deoxy-ribozyme for one hour. After incubation, aliquots of the reaction were used as templates for RT-PCR, amplifying regions including the targeted cleavage sites. The RT-PCR products were visualized on an ethidium bromide-containing 2% agarose gel under UV light, and the intensity of the products was determined as described above (FIG. 3). Those deoxy-ribozymes that were capable of cleaving the target mouse hairless mRNA with the highest efficiency were used for in vivo experiments (FIG. 3, lanes 1, 3).

Deoxy-ribozyme treatment schedule. Newborn C57B1/6J mice were treated with a deoxy-ribozyme formula twice a day starting on the first day after delivery. As the mice started to grow hair, hair shafts were regularly shortened using an electric clipper to make the skin surface accessible and to enhance the penetration of the treatment formula. For each treatment, 2 deoxy-ribozyme, dissolved in a 85% EtOH and 15% ethylene glycol vehicle, were applied to a one square centimeter area on the back. During application and for a fifteen minute period after, the mice were placed in temporary restraint to prevent removal of the formula. Control animals were treated with vehicle containing oligonucleotides of the same length but of random sequence. The treatment continued until the mice were sacrificed for evaluation.

Biopsy Procedures and Pathology. The mice were humanely euthanized after 28 days, 35 days or 8 weeks of treatment. The entire treatment area, together with an equal sized non-treated neighboring area of skin, were removed, fixed in formalin solution, embedded and processed for pathology using standard procedures.

Results

To evaluate the feasibility of using topically applied deoxy-ribozymes for selective ablation of genes expressed in the hair follicle, a model system was used to recapitulate the hairless mouse phenotype. After secondary structure based target-site selection, the choices were narrowed for targeting oligonucleotides using a novel in vitro cleavage assay (Cserhalmi-Friedman et al. manuscript in preparation). The three deoxy-ribozymes that proved to be the most efficient in cutting full-length mouse hairless mRNA in vitro were used for the in vivo experiments.

After continuous treatment, by day 20 the hair of the treated animals became visibly sparse on the treated area. Pathology specimens taken from the treated area at day 28 (see FIGS. 2A-2D) demonstrated (i) a decreased number of hair follicles, (ii) several dense, basophilic cell groups in the dermis corresponding to dermal papillae by morphology and localization, and (iii) an absence of surrounding epithelial hair follicle tissues and related hair follicles. The remaining hair follicles were in telogen phase, in sharp contrast with the advanced anagen follicles of the surrounding untreated skin and the skin of the untreated control animals.

Samples taken from the treated area at day 35 showed a different result. Some follicles in telogen phase could be observed, although they were more sparse than in the surrounding untreated area or in the samples from the untreated control animals. In the dermis of the treated region, large epithelial cysts filled with amorphous material were noticed, which corresponded to dermal cysts. These characteristics, the arrest of hair cycling, involution of hair follicles, detachment of dermal papillae and development of dermal cysts are not normally present in C57B1/6J mice, but represent the cardinal features of the skin of the hairless mouse.

The data revealed here demonstrate that by using topically applied catalytic oligonucleotides, a key player of hair follicle regulation can be eliminated and hair follicle cycling can be disrupted. These results serve not only as a proof of principle for future use of this approach for hair removal, but also demonstrate the feasibility of using topical catalytic nucleic acid technology to successfully change the gene expression pattern of hair follicle cells at the mRNA level, and thus influence the hair phenotype.

Part II—Antisense Nucleic Acids

Figure 4:
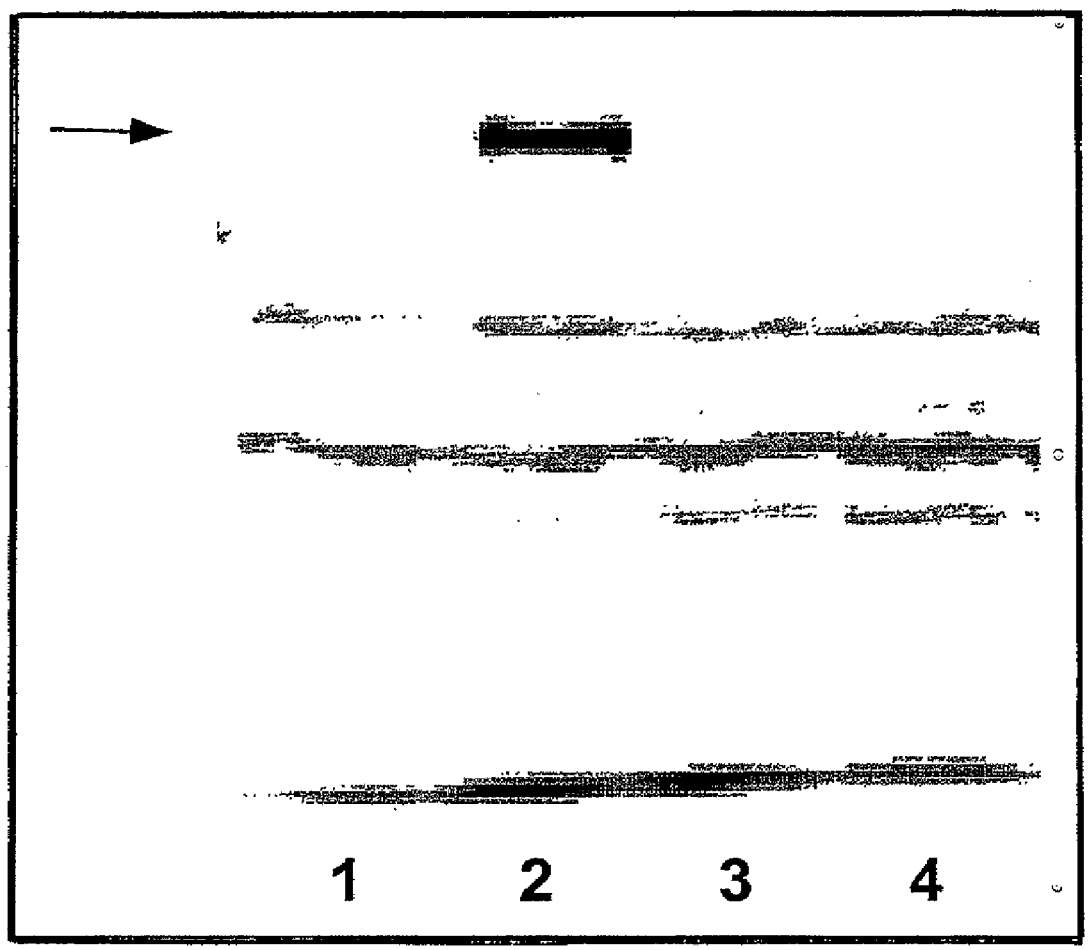
FIG. 4: This figure shows antisense oligonucleotide inhibition of Hairless Protein expression in Cos-1 cells. Lane 1 is the negative control where cells were not transfected with the full-length Hairless construct. Lane 2 shows Hairless expression in the positive control experiment where antisense oligonucleotides were not introduced. Lanes 3 and 4 show the inhibition of Hairless where anti-Hairless antisense ODN1

Antisense oligodeoxynucleotides were synthesized as directed to the inhibition of Hairless expression based on the Hairless mRNA sequence (SEQ ID NO:1). Cos-1 cells were transfected with the pEGFP full-length Hairless construct, and cells were harvested 16 hours after transfection. Total protein lysate was analyzed on a 10% SDS PAGE gel and transferred to nitrocellulose. Hairless protein was detected using an anti-Hairless polyclonal antibody raised against a C-terminal peptide. In a negative control, cells not transfected with the full-length Hairless construct showed no Hairless expression. Hairless expression was clearly observed in positive control experiments when antisense oligodeoxynucleotides were not added. Experiments where anti-Hairless antisense oligonucleotides (i.e. ODN1: 5' GCTGGGCATACTCTCCAT 3' (SEQ ID NO:26) and ODN2: 5' CATCACTCTCCTGCCCTC 3' (SEQ ID NO:27)) were added to the medium at 40 µM concentration prior to the transfection clearly showed an absence of Hairless expression, demonstrating antisense oligodeoxynucleotide inhibition of the Hairless gene product (see FIG. 4).

REFERENCES

Ahmad W, Faiyaz ul Haque M, Brancolini V, Tsou H C, ul Haque S, Lam H, Aita V M, Owen J, deBlaquiere M, Frank J, Cserhalmi-Friedman P B, Leask A, McGrath J A, Peacocke M, Ahmad M, Ott J, Christiano A M (1998a) Alopecia universalis associated with a mutation in the human hairless gene. Science 279:720-4.

Ahmad W, Panteleyev A A, Henson-Apollonio V, Sundberg J P, Christiano A M (1998b) Molecular basis of a novel rhino (hr(rhChr)) phenotype: a nonsense mutation in the mouse hairless gene. Exp Dermatol 7:298-301.

Bartel D P (1999) Creation and evolution of new ribozymes. Biol Bull 196:322-3.

Bertrand E, Castanotto D, Zhou C, Carbonnelle C, Lee N S, Good P, Chatterjee S, Grange T, Pictet R, Kohn D, Engelke D, Rossi J J (1997) The expression cassette determines the functional activity of ribozymes in mammalian cells by controlling their intracellular localization. RNA 3:75-88.

Cairns M J, King A, Sun L Q (2000) Nucleic acid mutation analysis using catalytic DNA. Nucleic Acids Res 28:E9.

Cech T R (1987) The chemistry of self-splicing RNA and RNA enzymes. Science 236:1532-9.

Fedor M J (2000) Structure and Function of the Hairpin Ribozyme. J Mol Biol 297 (2):269-91.

Flory C M, Pavco P A, Jarvis T C, Lesch M E, Wincott F E, Beigelman L, Hunt S W, 3rd, Schrier D J (1996) Nuclease-resistant ribozymes decrease stromelysin mRNA levels in rabbit synovium following exogenous delivery to the knee joint. Proc Natl Acad Sci USA 93:754-8.

Long M B, Sullenger B A (1999) Evaluating group I intron catalytic efficiency in mammalian cells. Mol Cell Biol 19: 6479-87.

Matzura O., Wennborg A (1996) RNAdraw: an integrated program for RNA secondary structure calculation and analysis under 32-bit Microsoft Windows. Comput Appl Biosci 12:247-9.

Michienzi A, Prislei S, Bozzoni I (1996) U1 small nuclear RNA chimeric ribozymes with substrate specificity for the Rev pre-mRNA of human immunodeficiency virus. Proc Natl Acad Sci USA 93:7219-24.

Montgomery R A, Dietz H C (1997) Inhibition of fibrillin 1 expression using U1 snRNA as a vehicle for the presentation of antisense targeting sequence. Hum Mol Genet 6:519-25.

Panteleyev A A, Ahmad W, Malashenko A M, Ignatieva E L, Paus R, Sundberg J P, Christian A M (1998a) Molecular basis for the rhino Yurlovo (hr(rh)) phenotype: severe skin abnormalities and female reproductive defects associated with an insertion in the hairless gene. Exp Dermatol 7: 281-8.

Panteleyev A A, Paus R, Ahmad W, Sundberg J P, Christiano A M (1998b) Molecular and functional aspects of the hairless (hr) gene in laboratory rodents and humans. Exp Dermatol 7:249-67.

Parthasarathy R, Cote G J, Gagel R F (1999) Hammerhead ribozyme-mediated inactivation of mutant RET in medullary thyroid carcinoma. Cancer Res 59:3911-4.

Pley et al, (1994) Three-dimensional structure of a hammerhead ribozyme. Nature 372:68-74.

Phylactou L A, Kilpatrick M W, Wood M J (1998) Ribozymes as therapeutic tools for genetic disease. Hum Mol Genet 7: 1649-53.

Sambrook et al., "Molecular Cloning: A Laboratory Manual", Second Edition (1989), Cold Spring Harbor Laboratory Press, Cold Spring Harbor, N.Y.

Santiago F S, Lowe H C, Kavurma M M, Chesterman C N, Baker A, Atkins D G, Khachigian L M (1999) New DNA enzyme targeting Egr-1 mRNA inhibits vascular smooth muscle proliferation and regrowth after injury. Nat Med 5:1438.

Santoro S W, Joyce G F (1997) A general purpose RNA-cleaving DNA enzyme. Proc Natl Acad Sci USA 94:4262-6.

Santoro S W, Joyce G F (1998) Mechanism and utility of an RNA-cleaving DNA enzyme. Biochemistry 37:13330-42.

Sioud M (1996) Ribozyme modulation of lipopolysaccharide-induced tumor necrosis factor-alpha production by peritoneal cells in vitro and in vivo. Eur J Immunol 26: 1026-31.

Sioud M, Drlica K (1991) Prevention of human immunodeficiency virus type 1 integrase expression in *Escherichia coli* by a ribozyme. Proc Natl Acad Sci USA 88: 7303-7.

Vaish N K, Kore A R, Eckstein F (1998) Recent developments in the hammerhead ribozyme field. Nucleic Acids Res 26: 5237-42.

What is claimed is:

1. An oligonucleotide that specifically hybridizes to Hairless Protein mRNA so as to inhibit the translation thereof in a cell, wherein the oligonucleotide comprises consecutive nucleotides having the sequence of SEQ ID NO:27.

2. A vector that expresses the oligonucleotide of claim 1.

3. A host-vector system comprising a cell having the vector of claim 2 therein.

4. A pharmaceutical composition comprising (a) the oligonucleotide of claim 1 or the vector of claim 2 and (b) a pharmaceutically acceptable carrier.

5. The pharmaceutical composition of claim 4, wherein the carrier is selected from the group consisting of an alcohol, ethylene glycol and a liposome.

6. The oligonucleotide of claim 1, wherein the Hairless Protein mRNA has the sequence as set forth in SEQ ID NO:1.

* * * * *

SEQUENCE LISTING

<160> NUMBER OF SEQ ID NOS: 27

<210> SEQ ID NO 1
<211> LENGTH: 5709
<212> TYPE: DNA
<213> ORGANISM: Homo sapiens

<400> SEQUENCE: 1

| | | | | | |
|---|---|---|---|---|---|
| tctcccggga | gccactcccc | tgggcgcctc | tccagcccct | gggctggaag | caccagcaac | 60 |
| cctggggatg | gggcagaccc | tcacagcccg | gggtctggag | ccgtgtcgg | agctcacatg | 120 |
| ggcccatgac | ctctccagac | atttggcaaa | atcaaggccc | ttagaccagg | gacagaccca | 180 |
| agcccaggcc | ctcccagagg | tcataggacg | caacccttg | tgcccttggg | ctatggaaga | 240 |
| ggtttgggaa | cggctttggg | gtggaagatg | gccaaaggag | cagcttggcc | aggtgaggat | 300 |
| gaggcagggc | agacacaggc | cagtggggcg | tgccatgtgc | cacagatgga | gaggaccagg | 360 |
| agccagtggc | ccggcaggca | cagcccggtt | ggcgtgggcc | agagcgccca | tcactgaccc | 420 |
| gtgagaactc | gactgcccct | gccagctctg | gcactgcccc | ctcccagccg | ccccgcccta | 480 |
| gcaccctggg | gggcaccccg | cccaaccgtg | gcctggtccg | gcccctcccg | cccttgctc | 540 |
| cagttcccgg | gcttggcacc | tatagtgggg | gtgccgcccg | cctgccaggc | tccggggccg | 600 |
| ggcccacggg | agggtgggc | ggctgggaag | ctggcacgct | gccccggggg | agcctctgtc | 660 |
| ggcaggcgcc | cgggtgccgc | ggggggagg | gggaacaaag | ggctcattct | ccccgtgcgc | 720 |
| agccggtggc | atcgccgggg | cgttggcgga | agccccggg | gccgggagg | gggccggccc | 780 |
| aggcgcggcc | gccgaatcac | gggctcctgt | ttcccgcagg | gtgctggagg | aggaaaccgg | 840 |
| cggagcagct | tccccactct | cagttgcgcg | tctggcgatg | gcgatcagag | gtcgtgctgc | 900 |
| gctctccgcc | gcgctctacc | tccattagcc | gcgctgcgcg | gtgctgcgcc | ctcgccggtg | 960 |
| cctctctcct | gggtcccagg | atcggccccc | accatccagg | cacgaccccc | ttccccggcc | 1020 |
| cctcggcctt | tccccaact | cggccatctc | cgacccgggg | cgcgtgttcc | ccccggcccg | 1080 |
| gcgccttctc | tccctccggg | ggcacccgct | ccctagcccc | ggcccggccc | tccccgcggc | 1140 |
| gcagcacgga | gtctcggcgt | cccatggcgc | aacctacggc | ctcggcccag | aagctggtgc | 1200 |
| ggccgatccg | cgccgtgtgc | cgcatcctgc | agatcccgga | gtccgacccc | tccaacctgc | 1260 |
| ggccctagag | cgcccccgcc | gccccggggg | aaggagagcg | cgagcgcgct | gagcagacag | 1320 |
| agcgggagaa | cgcgtcctcg | cccgccggcc | gggaggcccc | ggagctggcc | catggggagc | 1380 |
| aggcgcccgg | tgccggccac | gacgaccgcc | accgcccgcg | ccgcgaccgg | ccggtgaagc | 1440 |
| ccagggaccc | ccctctggga | gagccccatg | agggcaggag | agtgatggag | agtacgccca | 1500 |
| gcttcctgaa | gggcacccca | acctgggaga | agacggcccc | agagaacggc | atcgtgagac | 1560 |
| aggagcccgg | cagcccgcct | cgagatggac | tgcaccatgg | gccgctgtgc | ctgggagagc | 1620 |
| ctgctcccctt | ttggagggc | gtcctgagca | cccagactc | ctggcttccc | cctggcttcc | 1680 |
| cccagggccc | caaggacatg | ctcccacttg | tggaggcga | gggcccccag | aatgggagga | 1740 |
| ggaaggtcaa | ctggctgggc | agcaaagagg | gactgcgctg | gaaggaggcc | atgcttaccc | 1800 |
| atccgctggc | attctgcggg | ccagcgtgcc | cacctcgctg | tgccccctg | atgcctgagc | 1860 |
| atagtggtgg | ccatctcaag | agtgaccctg | tggccttccg | gccctggcac | tgcccttcc | 1920 |
| ttctggagac | caagatcctg | gagcgagctc | ccttctgggt | gccacctgc | ttgccaccct | 1980 |
| acctagtgtc | tggcctgccc | ccagagcatc | catgtgactg | gcccctgacc | ccgcacccct | 2040 |

-continued

```
gggtatactc cggggggccag cccaaagtgc cctctgcctt cagcttaggc agcaagggct    2100
tttactacaa ggatccgagc attcccaggt tggcaaagga gcccttggca gctgcggaac    2160
ctgggttgtt tggcttaaac tctggtgggc acctgcagag agccggggag ccgaacgcc     2220 cttcactgca ccagagggat ggagagatgg gagctggccg gcagcagaat ccttgcccgc    2280
tcttcctggg gcagccagac actgtgccct ggacctcctg gcccgcttgt ccccaggcc     2340 ttgttcatac tcttggcaac gtctgggctg gccaggcga tgggaacctt gggtaccagc     2400
tggggccacc agcaacacca aggtgcccct ctcctgagcc gcctgtcacc cagcggggct    2460
gctgttcatc ctacccaccc actaaaggtg gggatcttgg cccttgtggg aagtgccagg    2520
agggcctgga ggggggtgcc agtggagcca gcgaacccag cgaggaagtg aacaaggcct    2580
ctggccccag ggcctgtccc cccagccacc acaccaagct gaagaagaca tggctcacac    2640
ggcactcgga gcagtttgaa tgtccacgcg gctgccctga ggtcgaggag aggccggttg    2700
ctcggctccg ggccctcaaa agggcaggca gccccgaggt ccaggagca atgggcagtc     2760 cagcccccaa gcggccaccg gacccttttcc caggcactgc agaacagggg gctgggggtt   2820
ggcaggaggt gcgggacaca tcgataggga acaaggatgt ggactcggga cagcatgatg    2880
agcagaaagg accccaagat ggccaggcca gtctccagga cccgggactt caggacatac    2940
catgcctggc tctccctgca aaactggctc aatgccaaag ttgtgcccag gcagctggag    3000
agggaggagg gcacgcctgc cactctcagc aagtgcggag atcgcctctg ggaggggagc    3060
tgcagcagga ggaagacaca gccaccaact ccagctctga ggaaggccca gggtccggcc    3120
ctgacagccg gctcagcaca ggcctcgcca agcacctgct cagtggtttg ggggaccgac    3180
tgtgccgcct gctgcggagg gagcgggagg ccctggcttg gcccagcgg gaaggccaag     3240 ggccagccgt gacagaggac agcccaggca ttccacgctg ctgcagccgt tgccaccatg    3300
gactcttcaa cacccactgg cgatgtcccc gctgcagcca ccggctgtgt gtggcctgtg    3360
gtcgtgtggc aggcactggg cgggccaggg agaaagcagg cttttcaggag cagtccgcgg    3420 aggagtgcac gcaggaggcc gggcacgctg cctgttccct gatgctgacc cagtttgtct    3480
ccagccaggc tttggcagag ctgagcactg caatgcacca ggtctgggtc aagtttgata    3540
tccgggggca ctgccctgc caagctgatg cccgggtatg ggccccggg gatgcaggcc      3600 agcagaagga atcaacacag aaaacgcccc caactccaca accttcctgc aatggcgaca    3660
cccacaggac caagagcatc aaagaggaga ccccgattc cgctgagacc ccagcagagg     3720
accgtgctgg ccgagggccc ctgccttgtc cttctctctg cgaactgctg gcttctaccg    3780
cggtcaaact ctgcttgggc catgagcgaa tacacatggc cttcgccccc gtcactccgg    3840
ccctgcccag tgatgaccgc atcaccaaca tcctggacag cattatcgca caggtggtgg    3900
aacggaagat ccaggagaaa gccctggggc cggggcttcg agctggcccg ggtctgcgca    3960
agggcctggg cctgccccctc tctccagtgc ggccccggct gcctccccca ggggctttgc    4020
tgtggctgca ggagccccag ccttgccctc ggcgtggctt ccacctcttc caggagcact    4080
ggaggcaggg ccagcctgtg ttggtgtcag ggatccaaag gacattgcag ggcaacctgt    4140
gggggacaga agctcttggg gcacttggag gccaggtgca ggcgctgagc cccctcggac    4200
ctccccagcc cagcagcctg ggcagcacaa cattctggga gggcttctcc tggcctgagc    4260
ttcgcccaaa gtcagacgag ggctctgtcc tcctgctgca ccgagctttg ggggatgagg    4320
acaccagcag ggtggagaac ctagctgcca gtctgccact tccggagtac tgcgccctcc    4380
atggaaaact caacctggct tcctacctcc caccgggcct tgccctgcgt ccactggagc    4440
```

-continued

```
cccagctctg ggcagcctat ggtgtgagcc cgcaccgggg acacctgggg accaagaacc    4500
tctgtgtgga ggtggccgac ctggtcagca tcctggtgca tgccgacaca ccactgcctg    4560
cctggcaccg ggcacagaaa gacttccttt caggcctgga cggggagggg ctctggtctc    4620
cgggcagcca ggtcagcact gtgtggcacg tgttccgggc acaggacgcc cagcgcatcc    4680
gccgctttct ccagatggtg tgcccggccg gggcaggcgc cctggagcct ggcgcccag     4740 gcagctgcta cctggatgca gggctgcggc ggcgcctgcg ggaggagtgg ggcgtgagct    4800
gctggaccct gctccaggcc cccggagagg ccgtgctggt gcctgcaggg gctccccacc    4860
aggtgcaggg cctggtgagc acagtcagcg tcactcagca cttcctctcc cctgagacct    4920
ctgccctctc tgctcagctc tgccaccagg acccagcct  tcccctgac tgccacctgc    4980 tttatgccca gatggactgg gctgtgttcc aagcagtgaa ggtggccgtg gggacattac    5040
aggaggccaa atagagggat gctaggtgtc tgggatcggg gtggggacag gtagaccagg    5100
tgctcagccc aggcacaact tcagcagggg atggcgctag gggacttggg gatttctggt    5160 caacccaca agcaccactc tgggcacaag cagggcactc tgttcccctc ccccttaagc     5220
caacaaccac agtgccacca agctcacacc tgtccttctc aggctggcat ctcccccacc    5280
ctgtgcccct tttcatggta ccaggcccgc actgggggca attgacttcc tccaatcccc    5340
actcctccga gacccaggag acaaacagcc cttccttggg gaaacttggg aatcattctg    5400
gcttaaacaa cacctcctcc tgctgctcac tcccgctgag cccactctac tgccccagct    5460
ccgtttctac caccgcatcc tcactgggct cactgcaggc atgctgaaca aggggcctcc    5520
aaccttctgc cctcctgcca aaagatctgg ggagtgtgag gagagggtgg catcaggagc    5580
tgctcaggct tggcggaggg agcggcatgg gcgatgtcac tcatgccctt cccggtccgc    5640
ccgcttccct ccttcatgat ttccattaaa gtctgttgtt ttgaaaaaaa aaaaaaaaaa    5700
aaaaaaaaa                                                           5709
```

<210> SEQ ID NO 2
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 2
cccatggggc tagctacaac gagcagtcc                                      29

<210> SEQ ID NO 3
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy ribozyme

<400> SEQUENCE: 3
cggcccaggc tagctacaac gaggtgcag                                      29

<210> SEQ ID NO 4
<211> LENGTH: 29
<212> TYPE: DNA
<213> ORGANISM: Artificial Sequence
<220> FEATURE:
<221> NAME/KEY: misc_feature
<222> LOCATION: ()..()

-continued

```
<223> OTHER INFORMATION: deoxy ribozyme

<400> SEQUENCE: 4
ctcaggaggc tagctacaac gagcccctc                                    29

<210> SEQ ID NO 5
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 5
gggagcaggc tagctacaac gagtccttg                                    29

<210> SEQ ID NO 6
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 6
ctccccaggc tagctacaac gatctgggg                                    29

<210> SEQ ID NO 7
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 7
cagccagggc tagctacaac gatgacctt                                    29

<210> SEQ ID NO 8
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 8
cagcggaggc tagctacaac gagggtaag                                    29

<210> SEQ ID NO 9
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 9
cgcagaaggc tagctacaac gagccagcg                                    29

<210> SEQ ID NO 10
<211> LENGTH: 29
<212> TYPE: DNA
```

```
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 10 tgcgggggc tagctacaac gacaggggc                                29

<210> SEQ ID NO 11
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 11
aggggtgggc tagctacaac gaggggtca                                29

<210> SEQ ID NO 12
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 12
cccggagggc tagctacaac gaatcccca                                29

<210> SEQ ID NO 13
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 13
gcctaagggc tagctacaac gatgaaggc                                29

<210> SEQ ID NO 14
<211> LENGTH: 30
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 14
ggcaaggagg ctagctacaa cgatctgctg                               30

<210> SEQ ID NO 15
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 15
gttcccaggc tagctacaac gacgcctgg                                29
```

<210> SEQ ID NO 16
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: deoxy - ribozyme

<400> SEQUENCE: 16
cagctggggc tagctacaac gaacccaag                                    29

<210> SEQ ID NO 17
<211> LENGTH: 1189
<212> TYPE: PRT
<213> ORGANISM: Homo sapiens

<400> SEQUENCE: 17

```
Met Glu Ser Thr Pro Ser Phe Leu Lys Gly Thr Pro Thr Trp Glu Lys
1               5                   10                  15

Thr Ala Pro Glu Asn Gly Ile Val Arg Gln Glu Pro Gly Ser Pro Pro
            20                  25                  30

Arg Asp Gly Leu His His Gly Pro Leu Cys Leu Gly Glu Pro Ala Pro
        35                  40                  45

Phe Trp Arg Gly Val Leu Ser Thr Pro Asp Ser Trp Leu Pro Pro Gly
    50                  55                  60

Phe Pro Gln Gly Pro Lys Asp Met Leu Pro Leu Val Glu Gly Glu Gly
65                  70                  75                  80

Pro Gln Asn Gly Glu Arg Lys Val Asn Trp Leu Gly Ser Lys Glu Gly
                85                  90                  95

Leu Arg Trp Lys Glu Ala Met Leu Thr His Pro Leu Ala Phe Cys Gly
            100                 105                 110

Pro Ala Cys Pro Pro Arg Cys Gly Pro Leu Met Pro Glu His Ser Gly
        115                 120                 125

Gly His Leu Lys Ser Asp Pro Val Ala Phe Arg Pro Trp His Cys Pro
    130                 135                 140

Phe Leu Leu Glu Thr Lys Ile Leu Glu Arg Ala Pro Phe Trp Val Pro
145                 150                 155                 160

Thr Cys Leu Pro Pro Tyr Leu Val Ser Gly Leu Pro Pro Glu His Pro
                165                 170                 175

Cys Asp Trp Pro Leu Thr Pro His Pro Trp Val Tyr Ser Gly Gly Gln
            180                 185                 190

Pro Lys Val Pro Ser Ala Phe Ser Leu Gly Ser Lys Gly Phe Tyr Tyr
        195                 200                 205

Lys Asp Pro Ser Ile Pro Arg Leu Ala Lys Glu Pro Leu Ala Ala Ala
    210                 215                 220

Glu Pro Gly Leu Phe Gly Leu Asn Ser Gly Gly His Leu Gln Arg Ala
225                 230                 235                 240

Gly Glu Ala Glu Arg Pro Ser Leu His Gln Arg Asp Gly Glu Met Gly
                245                 250                 255

Ala Gly Arg Gln Gln Asn Pro Cys Pro Leu Phe Leu Gly Gln Pro Asp
            260                 265                 270

Thr Val Pro Trp Thr Ser Trp Pro Ala Cys Pro Gly Leu Val His
        275                 280                 285

Thr Leu Gly Asn Val Trp Ala Gly Pro Gly Asp Gly Asn Leu Gly Tyr
    290                 295                 300

Gln Leu Gly Pro Pro Ala Thr Pro Arg Cys Pro Ser Pro Glu Pro Pro
```

```
              305                 310                 315                 320
        Val Thr Gln Arg Gly Cys Cys Ser Ser Tyr Pro Thr Lys Gly Gly
                        325                 330                 335

Asp Leu Gly Pro Cys Gly Lys Cys Gln Glu Gly Leu Glu Gly Ala
                        340                 345                 350

Ser Gly Ala Ser Glu Pro Ser Glu Val Asn Lys Ala Ser Gly Pro
                        355                 360                 365

Arg Ala Cys Pro Pro Ser His His Thr Lys Leu Lys Lys Thr Trp Leu
                        370                 375                 380

Thr Arg His Ser Glu Gln Phe Glu Cys Pro Arg Gly Cys Pro Glu Val
        385                 390                 395                 400

Glu Glu Arg Pro Val Ala Arg Leu Arg Ala Leu Lys Arg Ala Gly Ser
                        405                 410                 415

Pro Glu Val Gln Gly Ala Met Gly Ser Pro Ala Pro Lys Arg Pro Pro
                        420                 425                 430

Asp Pro Phe Pro Gly Thr Ala Glu Gln Gly Ala Gly Gly Leu Gln Glu
                        435                 440                 445

Val Arg Asp Thr Ser Ile Gly Asn Lys Asp Val Asp Ser Gly Gln His
                        450                 455                 460

Asp Glu Gln Lys Gly Pro Gln Asp Gly Gln Ala Ser Leu Gln Asp Pro
        465                 470                 475                 480

Gly Leu Gln Asp Ile Pro Cys Leu Ala Leu Pro Ala Lys Leu Ala Gln
                        485                 490                 495

Cys Gln Ser Cys Ala Gln Ala Ala Gly Glu Gly Gly His Ala Cys
                        500                 505                 510

His Ser Gln Gln Val Arg Arg Ser Pro Leu Gly Gly Glu Leu Gln Gln
                        515                 520                 525

Glu Glu Asp Thr Ala Thr Asn Ser Ser Ser Glu Glu Gly Pro Gly Ser
                        530                 535                 540

Gly Pro Asp Ser Arg Leu Ser Thr Gly Leu Ala Lys His Leu Leu Ser
        545                 550                 555                 560

Gly Leu Gly Asp Arg Leu Cys Arg Leu Leu Arg Arg Glu Arg Glu Ala
                        565                 570                 575

Leu Ala Trp Ala Gln Arg Glu Ser Gln Gly Pro Ala Val Thr Glu Asp
                        580                 585                 590

Ser Pro Gly Ile Pro Arg Cys Cys Ser Arg Cys His His Gly Leu Phe
                        595                 600                 605

Asn Thr His Trp Arg Cys Pro Arg Cys Ser His Arg Leu Cys Val Ala
                        610                 615                 620

Cys Gly Arg Val Ala Gly Thr Gly Arg Ala Arg Glu Lys Ala Gly Phe
        625                 630                 635                 640

Gln Glu Gln Ser Ala Glu Glu Cys Thr Gln Glu Ala Gly His Ala Ala
                        645                 650                 655

Cys Ser Leu Met Leu Thr Gln Phe Val Ser Ser Gln Ala Leu Ala Glu
                        660                 665                 670

Leu Ser Thr Ala Met His Gln Val Trp Val Lys Phe Asp Ile Arg Gly
                        675                 680                 685

His Cys Pro Cys Gln Ala Asp Ala Arg Val Trp Ala Pro Gly Asp Ala
                        690                 695                 700

Gly Gln Gln Lys Glu Ser Thr Gln Lys Thr Pro Pro Thr Pro Gln Pro
        705                 710                 715                 720

Ser Cys Asn Gly Asp Thr His Arg Thr Lys Ser Ile Lys Glu Glu Thr
                        725                 730                 735
```

```
                                     -continued

Pro Asp Ser Ala Glu Thr Pro Ala Glu Asp Arg Ala Gly Arg Gly Pro
            740                 745                 750

Leu Pro Cys Pro Ser Leu Cys Glu Leu Leu Ala Ser Thr Ala Val Lys
            755                 760                 765

Leu Cys Leu Gly His Glu Arg Ile His Met Ala Phe Ala Pro Val Thr
            770                 775                 780

Pro Ala Leu Pro Ser Asp Asp Arg Ile Thr Asn Ile Leu Asp Ser Ile
785                 790                 795                 800

Ile Ala Gln Val Val Glu Arg Lys Ile Gln Glu Lys Ala Leu Gly Pro
                805                 810                 815

Gly Leu Arg Ala Gly Pro Gly Leu Arg Lys Gly Leu Gly Leu Pro Leu
            820                 825                 830

Ser Pro Val Arg Pro Arg Leu Pro Pro Gly Ala Leu Leu Trp Leu
            835                 840                 845

Gln Glu Pro Gln Pro Cys Pro Arg Arg Gly Phe His Leu Phe Gln Glu
            850                 855                 860

His Trp Arg Gln Gly Gln Pro Val Leu Val Ser Gly Ile Gln Arg Thr
865                 870                 875                 880

Leu Gln Gly Asn Leu Trp Gly Thr Glu Ala Leu Gly Ala Leu Gly Gly
                885                 890                 895

Gln Val Gln Ala Leu Ser Pro Leu Gly Pro Pro Gln Pro Ser Ser Leu
            900                 905                 910

Gly Ser Thr Thr Phe Trp Glu Gly Phe Ser Trp Pro Glu Leu Arg Pro
            915                 920                 925

Lys Ser Asp Glu Gly Ser Val Leu Leu Leu His Arg Ala Leu Gly Asp
            930                 935                 940

Glu Asp Thr Ser Arg Val Glu Asn Leu Ala Ala Ser Leu Pro Leu Pro
945                 950                 955                 960

Glu Tyr Cys Ala Leu His Gly Lys Leu Asn Leu Ala Ser Tyr Leu Pro
                965                 970                 975

Pro Gly Leu Ala Leu Arg Pro Leu Glu Pro Gln Leu Trp Ala Ala Tyr
            980                 985                 990

Gly Val Ser Pro His Arg Gly His  Leu Gly Thr Lys Asn  Leu Cys Val
            995                 1000                1005

Glu Val  Ala Asp Leu Val Ser  Ile Leu Val His Ala  Asp Thr Pro
            1010                1015                1020

Leu Pro  Ala Trp His Arg Ala  Gln Lys Asp Phe Leu  Ser Gly Leu
            1025                1030                1035

Asp Gly  Glu Gly Leu Trp Ser  Pro Gly Ser Gln Val  Ser Thr Val
            1040                1045                1050

Trp His  Val Phe Arg Ala Gln  Asp Ala Gln Arg Ile  Arg Arg Phe
            1055                1060                1065

Leu Gln  Met Val Cys Pro Ala  Gly Ala Gly Ala Leu  Glu Pro Gly
            1070                1075                1080

Ala Pro  Gly Ser Cys Tyr Leu  Asp Ala Gly Leu Arg  Arg Arg Leu
            1085                1090                1095

Arg Glu  Glu Trp Gly Val Ser  Cys Trp Thr Leu Leu  Gln Ala Pro
            1100                1105                1110

Gly Glu  Ala Val Leu Val Pro  Ala Gly Ala Pro His  Gln Val Gln
            1115                1120                1125

Gly Leu  Val Ser Thr Val Ser  Val Thr Gln His Phe  Leu Ser Pro
            1130                1135                1140

Glu Thr  Ser Ala Leu Ser Ala  Gln Leu Cys His Gln  Gly Pro Ser
            1145                1150                1155
```

Leu Pro  Pro Asp Cys His Leu  Leu Tyr Ala Gln Met  Asp Trp Ala
    1160              1165                 1170

Val Phe  Gln Ala Val Lys Val  Ala Val Gly Thr Leu  Gln Glu Ala
    1175              1180                 1185

Lys

<210> SEQ ID NO 18
<211> LENGTH: 15
<212> TYPE: DNA
<213> ORGANISM: Artificial Sequence
<220> FEATURE:
<221> NAME/KEY: misc_feature
<222> LOCATION: ()..()
<223> OTHER INFORMATION: Catalytic domain

<400> SEQUENCE: 18
ggctagctac aacga                                                      15

<210> SEQ ID NO 19
<211> LENGTH: 25
<212> TYPE: DNA
<213> ORGANISM: Artificial Sequence
<220> FEATURE:
<221> NAME/KEY: misc_feature
<222> LOCATION: ()..()
<223> OTHER INFORMATION: Catalytic domain

<400> SEQUENCE: 19
ctgatgagtc cgtgaggacg aaaca                                           25

<210> SEQ ID NO 20
<211> LENGTH: 56
<212> TYPE: DNA
<213> ORGANISM: Artificial Sequence
<220> FEATURE:
<221> NAME/KEY: misc_feature
<222> LOCATION: ()..()
<223> OTHER INFORMATION: Ribozyme

<400> SEQUENCE: 20
cggccggcgg gcgagctgat gagtccgtga ggacgaaaca cgcgttctcc cgctct        56

<210> SEQ ID NO 21
<211> LENGTH: 58
<212> TYPE: DNA
<213> ORGANISM: Artificial Sequence
<220> FEATURE:
<221> NAME/KEY: misc_feature
<222> LOCATION: ()..()
<223> OTHER INFORMATION: Ribozyme

<400> SEQUENCE: 21
gagtctgggg tgctcagctg atgagtccgt gaggacgaaa cacgcccctc caaaaagg     58

<210> SEQ ID NO 22
<211> LENGTH: 58
<212> TYPE: DNA
<213> ORGANISM: Artificial Sequence
<220> FEATURE:
<221> NAME/KEY: misc_feature
<222> LOCATION: ()..()
<223> OTHER INFORMATION: Ribozyme

<400> SEQUENCE: 22
ttgctgccca gccagttctg atgagtccgt gaggacgaaa caccttcctc tccccatt     58

```
<210> SEQ ID NO 23
<211> LENGTH: 58
<212> TYPE: DNA
<213> ORGANISM: Artificial Sequence
<220> FEATURE:
<221> NAME/KEY: misc_feature
<222> LOCATION: ()..()
<223> OTHER INFORMATION: Ribozyme

<400> SEQUENCE: 23
gctctggggg caggccactg atgagtccgt gaggacgaaa cacactaggt agggtggc      58

<210> SEQ ID NO 24
<211> LENGTH: 58
<212> TYPE: DNA
<213> ORGANISM: Artificial Sequence
<220> FEATURE:
<221> NAME/KEY: misc_feature
<222> LOCATION: ()..()
<223> OTHER INFORMATION: Ribozyme

<400> SEQUENCE: 24
atgaacaagg cctggggctg atgagtccgt gaggacgaaa cacaagcggg ccaggagg      58

<210> SEQ ID NO 25
<211> LENGTH: 58
<212> TYPE: DNA
<213> ORGANISM: Artificial Sequence
<220> FEATURE:
<221> NAME/KEY: misc_feature
<222> LOCATION: ()..()
<223> OTHER INFORMATION: Ribozyme

<400> SEQUENCE: 25
tcgcctggcc cagcccactg atgagtccgt gaggacgaaa cacgttgcca agagtatg      58

<210> SEQ ID NO 26
<211> LENGTH: 18
<212> TYPE: DNA
<213> ORGANISM: ARTIFICIALSEQUENCE
<220> FEATURE:
<221> NAME/KEY: misc_feature
<222> LOCATION: ()..()
<223> OTHER INFORMATION: ANTISENSEOLIGONUCLEOTIDEDIRECTED AT HUMAN
      HAIRLESS

<400> SEQUENCE: 26
gctgggcata ctctccat                                                  18

<210> SEQ ID NO 27
<211> LENGTH: 18
<212> TYPE: DNA
<213> ORGANISM: ARTIFICIAL SEQUENCE
<220> FEATURE:
<221> NAME/KEY: misc_feature
<222> LOCATION: ()..()
<223> OTHER INFORMATION: ANTISENSE OLIGONUCLEOTIDE DIRECTED AT HUMAN
      HAIRLESS

<400> SEQUENCE: 27
catcactctc ctgccctc                                                  18
```